(12) United States Patent
Akiba (10) Patent No.: US 6,984,204 B2
(45) Date of Patent: Jan. 10, 2006

(54) LIQUID FEED DEVICE FOR USE ON ENDOSCOPES

(75) Inventor: Haruo Akiba, Saitama (JP)

(73) Assignee: Fujinon Corporation, Saitama (JP)

( * ) Notice: Subject to any disclaimer, the term of this patent is extended or adjusted under 35 U.S.C. 154(b) by 163 days.

(21) Appl. No.: 10/689,607

(22) Filed: Oct. 22, 2003

(65) Prior Publication Data

US 2005/0096504 A1   May 5, 2005

(30) Foreign Application Priority Data

Oct. 23, 2002   (JP) .............................. 2002-308177

(51) Int. Cl.
*A61B 1/12*   (2006.01)

(52) U.S. Cl. .................... 600/158; 600/154; 251/149; 251/149.1

(58) Field of Classification Search ................ 600/104, 600/154, 158; 251/142, 149.1, 149.2
See application file for complete search history.

(56) References Cited

U.S. PATENT DOCUMENTS 4,649,904 A  *  3/1987  Krauter et al. .............. 600/154
5,114,408 A  *  5/1992  Fleischhaker et al. . 604/167.04
5,685,858 A  * 11/1997  Kawand ..................... 604/171

* cited by examiner

*Primary Examiner*—Linda C. M. Dvorak
*Assistant Examiner*—Matthew J. Kasztejna
(74) *Attorney, Agent, or Firm*—Oblon, Spivak, McClelland, Maier & Neustadt, P.C.

(57) ABSTRACT

An endoscopic liquid feed device to be fitted on a mouth piece of a liquid feed port which is provided on a casing of a manipulating head assembly of an endoscope in communication with an internal liquid feed passage leading to a liquid injection port at a distal end of an insertion tube of the endoscope for injecting a liquid into a body cavity. A liquid feed adaptor is detachably fitted on the mouth piece of the liquid feed port. The liquid feed adaptor is largely constituted by a Luer-Lok member having a check valve member fitted on a fore end portion thereof, a stopper ring fitted on the outer periphery of the Luer-Lok member, and a nut member rotatably fitted on the Luer-Lok member for axial displacements between the stopper ring and a flange portion provided at the outer proximal end of the Luer-Lok member. The nut member is threaded on an external screw provided on the outer periphery of the mouth piece. A Luer-Lok portion is provided within the mouth piece, and, in place of the liquid feed adaptor, a wash liquid syringe can be connected to the Luer-Lok portion of the mouth piece at the time of washing the internal liquid feed passage of the endoscope.

12 Claims, 7 Drawing Sheets

LIQUID FEED DEVICE FOR USE ON ENDOSCOPES

BACKGROUND OF THE INVENTION

1. Field of the Art

This invention relates to a liquid feed device for use on endoscopes, and more particularly to a liquid feed device which is especially suitable for use on endoscopes as an auxiliary water feed mechanism for spurting a jet of water or other liquids from a liquid injection port opened at a distal end of an endoscopic insertion tube.

2. Prior Art

Generally, a plural number of water feed/discharge means are provided on endoscopes. A first example is a body fluid suction or aspiration means. As a body fluid suction means, normally a suction passage is connected to a biopsy channel within an insertion tube of an endoscope, and a vacuum pump or a suction device is connected to the proximal end of the suction passage. At the time of aspiration, a suction valve which is provided on a manipulating head assembly of the endoscope is operated by an operator.

Further, generally a wash fluid or cleaning fluid feed means is provided on endoscopes for the purpose of sprinkling a cleaning fluid on an endoscopic observation window which is provided on a rigid tip end section at the distal end of the insertion tube. A cleaning liquid (normally wash water) and compressed air are generally employed as cleaning fluids. When an observation window is smudged with contaminants, firstly a cleaning liquid is spurted on the observation window to wash away deposited contaminants and then compressed air is blasted to remove droplets of the cleaning liquid. Therefore, an air feed passage is provided on an endoscope along with a liquid feed passage. Air/water feed valves which are provided on the manipulating head assembly of the endoscope are operated at the time of feeding a cleaning liquid or compressed air through the liquid feed passage or the air feed passage. At a point in the vicinity of the distal end portion of the insertion tube, the liquid feed passage and the air feed passage are joined together into a joined fluid passage leading to a nozzle which is provided on a tip end section of the insertion tube to spurt a cleaning fluid toward the observation window of the endoscope. Firstly, a cleaning liquid is supplied to the nozzle through the liquid feed passage and the joined fluid passage by putting the air/water feed valve in a liquid feed position. Then, the air/liquid feed valve is switched to an air feed position for spurting out compressed air from the nozzle through the air feed passage and the joined fluid passage. Therefore, when an observation window at the distal end of an insertion tube is smudged with contaminants, it can be washed clean without extracting the insertion tube from a body cavity.

Further, still another liquid feed device is incorporated in some endoscopes for spurting water into a body cavity under high pressure for the purpose of washing intracavitary walls or for sprinkling a coloring pigment or other liquid or solutions. This liquid feed device has a liquid injection hole or port opened at a distal end of the insertion tube to spurt a jet of a necessary liquid into a body cavity. In this case, a liquid is spurted in the direction of a view filed of the observation window of the endoscope, different from the above-mentioned cleaning liquid which is spurted toward and on the endoscopic observation window itself.

As described above, the liquid feed device is provided with a liquid injection port at the distal end of the insertion tube. As pressurized liquid feed means to be employed for sending a liquid under pressure, a syringe or a liquid pumping means is detachably connected to a liquid feed port which is provided on the casing of the manipulating head assembly of the endoscope. The liquid feed port is connected with the liquid injection port by a flexible tube internally providing a liquid feed passage. Normally, the pressure within a body cavity is higher than the atmospheric pressure. Therefore, there is possibilities of a liquid in the liquid feed passage or fluids in a body cavity flowing in a reverse direction, that is, in an outward direction and flowing out of the liquid inlet. In order to prevent this, the liquid feed port has to be retained in a closed state when no liquid is fed to the liquid feed passage. More particularly, for this purpose, a check valve is provided on the side of the liquid feeder, thereby normally blocking communication between the liquid feed passage and the atmosphere. When a pressurized liquid feed means is connected to feed a liquid under high pressure, the check valve is opened to permit supply of the liquid toward the liquid injection port through the liquid feed passage.

An endoscope has to be washed and disinfected each time after use. In washing and disinfecting a used endoscope, it is important to reprocess not only the liquid injection port which is opened at the distal end of the insertion tube, but also internal portions of the liquid feed passage which is in communication with the liquid injection port. A cleaning liquid and a disinfectant liquid are fed under pressure toward the liquid supply passage and the liquid injection port by connecting a syringe or a pressurized liquid feed means which is filled with a cleaning liquid or a disinfectant. In some cases, the liquid injection port and the liquid feed passage are scrubbed by inserting a brush into the liquid feed passage through the liquid injection port.

However, the check valve which is provided on the side of a liquid feed device becomes an obstacle in a washing operation, more specifically, an obstacle to the supply of cleaning and disinfectant liquids in a washing operation or to the insertion of a cleaning brush in a scrubbing operation. Therefore, as known from Japanese Patent No. 2980232, for example, there have been introduced endoscopic liquid feed devices employing a detachable check valve on the side of a liquid feed port.

The above-mentioned Japanese patent shows arrangements, in which either a valve member of a check valve of the liquid feeder is detachably fitted in a liquid feed passage, or a passage forming member with a check valve is threaded into a female screw portion in a mouth piece of a liquid feeder.

In a case where a valve member is detachably fitted in a liquid feed passage as in the above-mentioned Japanese patent, there is a problem of damages to the valve member, caused by a hooking jig which is necessarily used at the time of forcibly mounting or dismantling the valve member into or out of the liquid feed passage. On the other hand, in a case where a check valve is built in a passage forming member to be threaded into a mouth piece of a liquid feeder, the existence of the female screw on the inner periphery of the mouth piece makes it difficult to connect a syringe of a cleaning liquid or a disinfectant for washing the liquid feed passage up to the liquid injection port at the distal end of the insertion tube.

SUMMARY OF THE INVENTION

In view of the foregoing situations, it is an object of the present invention to provide an endoscopic liquid feed device through which a liquid can be fed to a body cavity from a pressurized liquid feed means, no matter whether or not a check valve is mounted or dismantled.

According to the present invention, in order to achieve the above-stated objective, there is provided an endoscopic liquid feed device, the liquid feed device including a liquid feed port provided on a casing of a manipulating head assembly of an endoscope in communication with an internal liquid feed passage leading to a liquid injection port opened at a fore distal end portion of an insertion tube of the endoscope, and a mouth piece provided fixedly at the liquid feed port for detachably connecting a liquid feed adaptor to the liquid feed port at the time of feeding a liquid to the liquid injection port from a pressurized liquid feed means connected to the liquid feed adaptor, characterized in that: the liquid feed adaptor is constituted by a Luer-Lok member having a check valve member fitted on a fore end portion thereof, a stopper ring provided on outer periphery of the Luer-Lok member, and a nut member rotatably fitted on the Luer-Lok member and axially movable between the stopper ring and a flange portion provided at an outer proximal end of the Luer-Lok member; the mouth piece being provided with an external male screw portion on outer peripheral side thereof for threaded engagement with the nut member, and formed with a Luer-Lok portion on inner peripheral side thereof, the Luer-Lok portion having a gradually diminishing inside diameter in a forward direction; and a pressurized liquid feed means such as a syringe being detachably connectible to the Luer-Lok portion of the mouth piece in place of the liquid feed adaptor.

Generally, for injecting wash water or sprinkling a medicinal solution into a body cavity, a syringe is connected to a mouth piece at a liquid feed port. It is the usual practice to use a Luer-Lok member for detachably connecting a syringe to the mouth piece of the liquid feed port. Inner peripheral surface of the Luer-Lok member is tapered with a small taper angle to have a gradually diminishing diameter in a forward direction, and a syringe is diengageably fitted into such Luer-Lok member. A Luer-Lok portion is provided also on the mouth piece of the liquid feed port to permit connection thereto of a wash liquid syringe. The check valve member is fitted on a front end portion of the liquid feed adaptor. The check valve member is formed of rubber or similar resilient material, and contains a normally closed slit. The resilient material which constitutes the check valve member is utilized as a seal means in those portions where the liquid feed adaptor is in fitting engagement with the mouth piece of the liquid feed port. More particularly, a resilient seal portion which is provided continuously from the check valve member is pressed against the Luer-Lok taper surface of the mouth piece to form a hermetical seal between the liquid feed adaptor and the mouth piece.

For fixing the liquid feed adaptor to the mouth piece at the liquid feed port, the nut member on the liquid feed adaptor is adapted to be threaded on an external male screw portion which is provided on the outer periphery of the mouth piece. In this case, preferably multiple thread screws are employed for the male and female screw portions on the mouth piece and the nut member, so that the liquid feed adaptor can be securely fastened to the mouth piece by a reduced number of turns. The casing of the manipulating head assembly of the endoscope is arranged to circumvent and cover up the male screw portion on the outer periphery of the mouth piece which would otherwise be exposed to the outside.

The nut member is rotatable relative to the Luer-Lok member but assembled in such a manner as to prevent its separation from the Luer-Lok member. More particularly, for this purpose, the flange portion which is provided at the outer proximal end of the Luer-Lok member serves as a stopper on one side. On the other hand, the above-mentioned stopper ring on the Luer-Lok member prevents dislocation of the nut member in the forward direction. The stopper ring can be fixed to the Luer-Lok member by various methods. In this regard, the stopper ring can be threaded onto the outer periphery of the Luer-Lok member and then bonded to the latter by the use of an adhesive. Further, when the liquid feed adaptor is fitted on the mouth piece at the liquid feed port, it is necessary to prevent spontaneous rotational movements of the liquid feed adaptor and the stopper ring. For this purpose, rotational movements of the liquid feed adaptor and the stopper ring can be blocked, for example, by engaging axial projections and notched grooves which are provided on meeting end faces of the stopper ring and the mouth piece or vice versa. In a case where fore ends of the axial projections are rounded off into an arcuate shape, the axial projections are automatically guided into position for engagement with the notched grooves in an assured manner.

The above and other objects, features and advantages of the present invention will become apparent from the following particular description of the invention, taken in conjunction with the accompanying drawings. The accompanying drawings show by way of example some preferred embodiments of the present invention. Needless to say, the present invention should not be construed as being limited to the particular forms shown in the drawings.

DESCRIPTION OF PREFERRED EMBODIMENTS

Hereafter, the present invention is described more particularly by way of its preferred embodiment with reference to the accompanying drawings. Firstly, referring to FIG. 1, there is schematically shown general layout of a flexible endoscope to which the present invention is applicable. In that figure, indicated at 1 is a manipulating head assembly of the endoscope, at 2 an insertion tube to be introduced into a body cavity, and at 3 a universal cable. The insertion tube 2 includes an elongated flexible portion 2a, an angle section 2b and a rigid tip end section 2c. For turning the rigid tip end section 2c into a desired direction, the angle section 2b can be bent in an arbitrary direction by manipulation of an angulation control means 4 which is provided on the manipulating head assembly 1.

Figure 1:
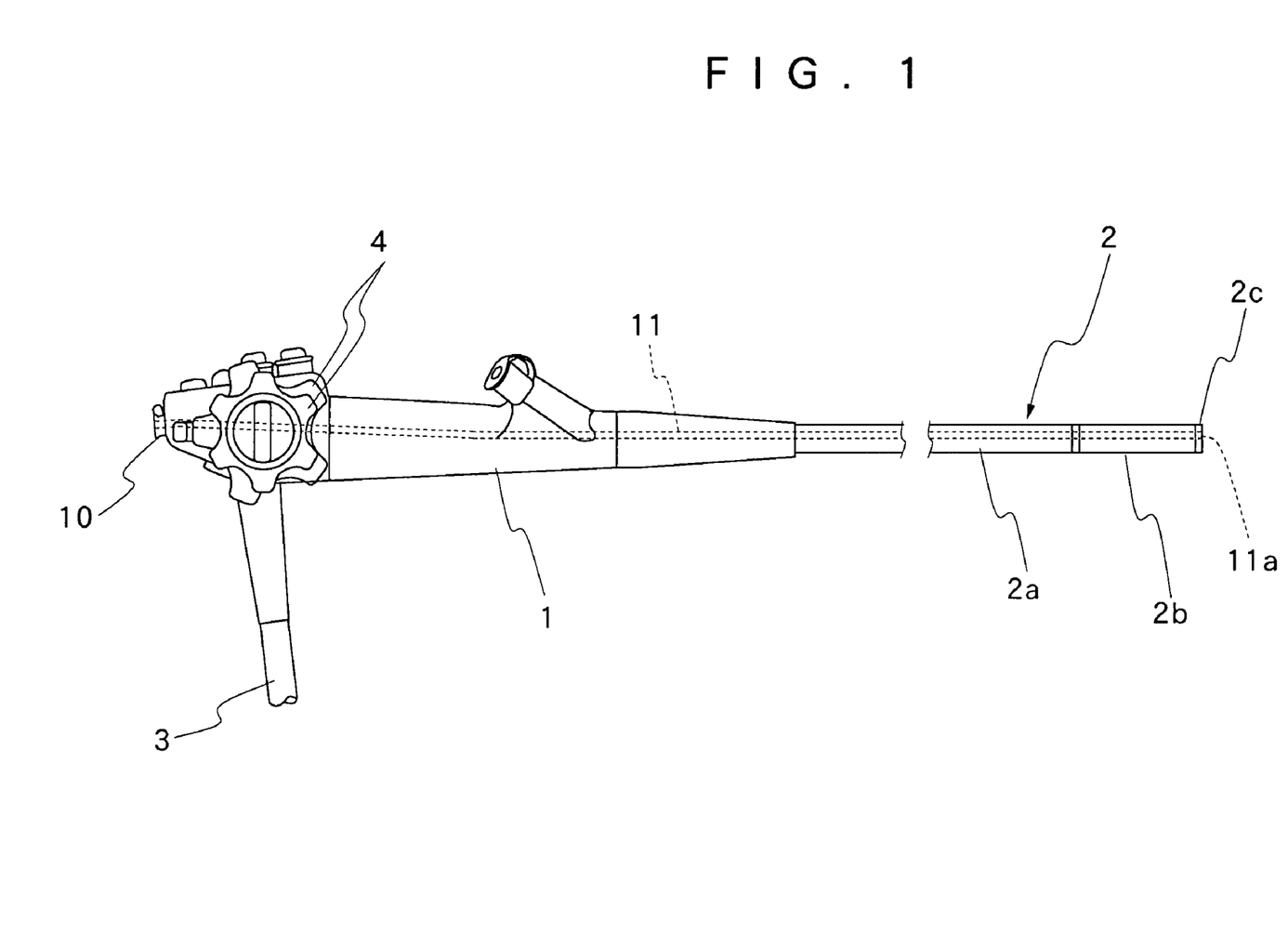
FIG. 1 is a schematic illustration of an endoscope employing a liquid feed device according to the present invention.

The endoscope is equipped with a liquid feed device which is also referred to as a jet injector or an auxiliary water feeder. Such water feed device includes a liquid feed port 10 which is provided on the casing of the manipulating head assembly 1, and a liquid feed passage 11 which is connected to the liquid feed port 10. The fore end of the liquid feed passage 11 is extended to a liquid injection port 11a which is opened on the rigid tip end section 2c of the insertion tube 2, at a position in the vicinity of an endoscopic observation meas which is built in the rigid tip end section 2c. In this instance, the liquid feed device is arranged to spurt a jet of water or a medicinal liquid toward an intracavitary wall surface. The liquid feed port 10 is provided on the back side of the manipulating head assembly 1, away from the front side to which the insertion tube 2 is connected. Therefore, within the manipulating head assembly 1, the liquid feed passage 11 can be extended substantially in a straightforward direction from the liquid feed port 10 for the purpose of facilitating insertion of a cleaning brush at the time of a washing operation. However, if desired, the liquid feed port 10 can be located on the lower side of the casing of the manipulating head assembly 1.

Figure 2:
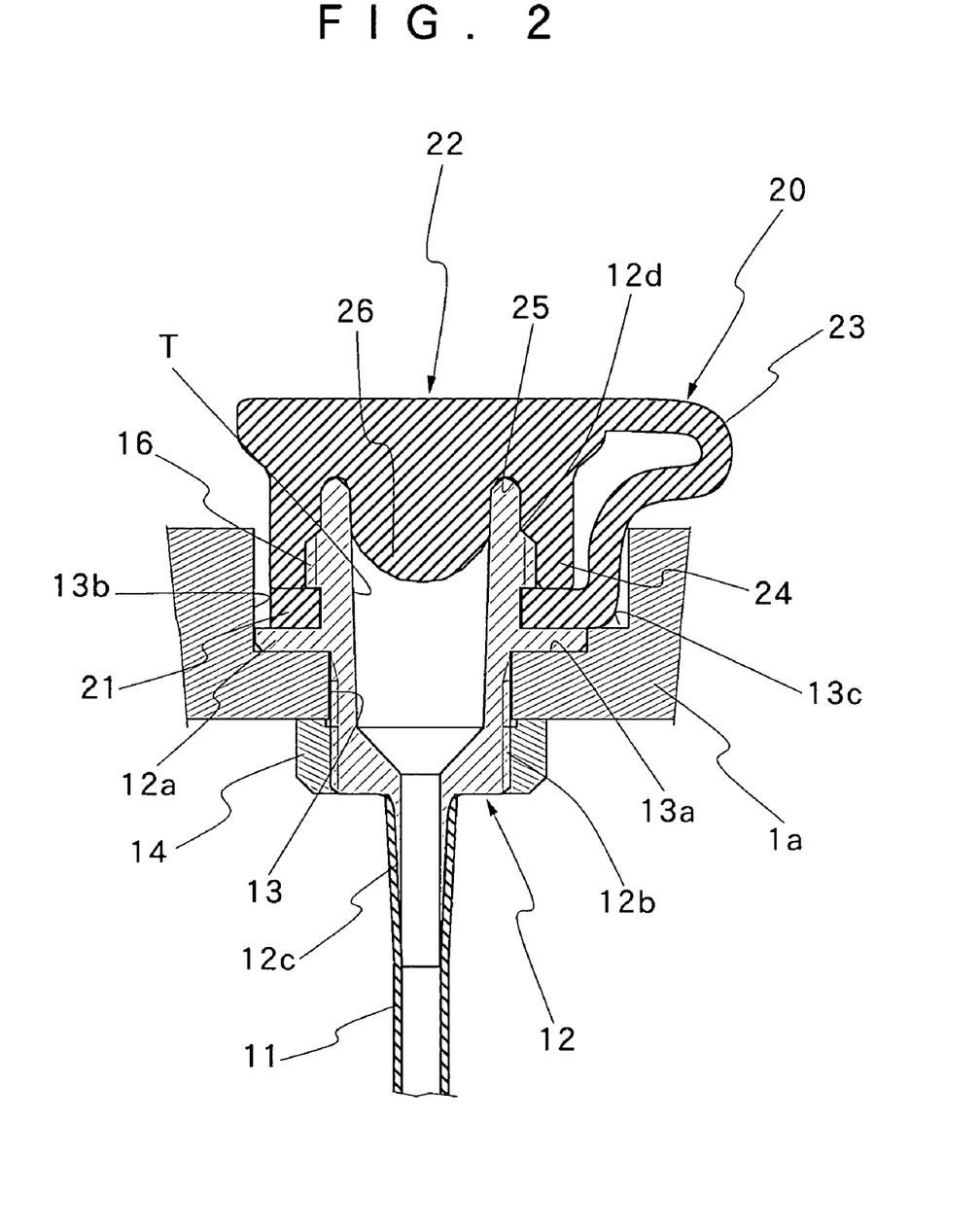
FIG. 2 is a schematic sectional view of a plug member fitted on a mouth piece of a liquid feed port on the endoscope.
Figure 3:
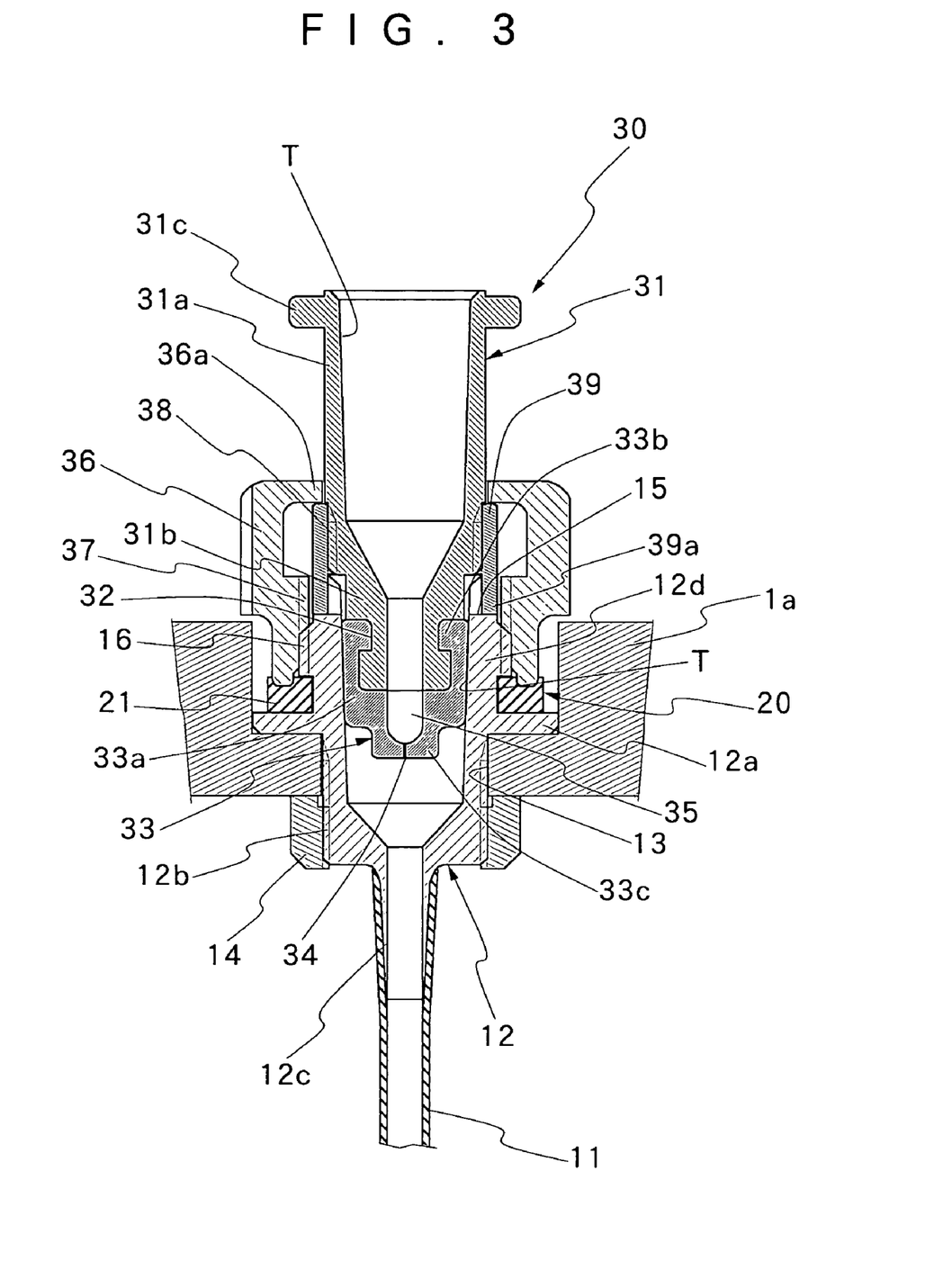
FIG. 3 is a schematic sectional view of a liquid feed adaptor fitted on a mouth piece of the liquid feed port.

As shown in FIGS. 2 and 3, the liquid feed port 10 is provided with a funnel-like mouth piece 12,. This mouth piece 12 is fixedly fitted in a nest hole 13 which is bored through a casing 1a of the manipulating head assembly 1. The mouth piece 12 is provided with a flange portion 12a to be abutted against stepped wall portions 13a of the nest hole 13. Further, the mouth piece 12 is provided with an external screw portion 12b on a cylindrical body portion on a front or inner side of the flange portion 12a, and an anchor nut 14 is threaded on the external screw portion 12b. Thus, the mouth piece 12 is fixed in position within the nest hole 13 by the flange portion 12a which firmly grips the casing 1a in cooperation with the anchor nut 14. Moreover, the mouth piece 12 is provided with a tubular connecting portion 12c centrally at its inner end of the externally threaded body portion 12b. The tubular connecting portion 12c is fitted in a base end portion of a tube which constitutes the liquid feed passage 11.

The mouth piece 12 is provided with a Luer-Lok portion 12d at its outer proximal end which is opened to the outside. In this instance, the Luer-Lok portion 12d is provided with a Luer-Lok taper surface T on its inner periphery in such a way that its inside diameter decreases continuously from the outer proximal end. The taper angle of this Luer-Lok taper surface T as moderate as 6/100. Furthermore, the Luer-Lok portion 12d is projected in an arcuate shape at its outer or proximal end, and provided with one or a plural number of notched grooves 15 at predetermined angular intervals in the circumferential direction (two notched grooves at intervals of 180 degrees in the case of the particular embodiment shown). Further, a male screw portion 16 is provided on the outer periphery of the Luer-Lok portion 12d at a position which is axially spaced position from the flange portion 12a by a predetermined distance. This male screw portion 16 is in the form of a multiple thread screw, for example, in the form of a double thread screw.

The outer proximal end of the mouth piece 12 is in an open state. Therefore, when the insertion tube 2 is introduced into a body cavity, the interior of the body cavity can be communicated with the atmosphere through the liquid feed port 10, liquid feed passage 11 and liquid injection port 11a. In order to avoid this, a plug member 20 or a liquid feed adaptor 30 is detachably fitted on the Luer-Lok portion 12d thereby to block communication between a body cavity and the atmosphere. In this connection, when the plug member 20 fitted on as shown in FIG. 2, the outer open end of the mouth piece 12 is closed, making a liquid feed operation infeasible. On the other hand, when the plug member 20 is removed and the liquid feed adaptor is fitted on the Luer-Lok portion 12d as shown in FIG. 3, it becomes possible to feed a liquid to a body cavity from a syringe to the liquid feed adaptor 30.

Figure 4:
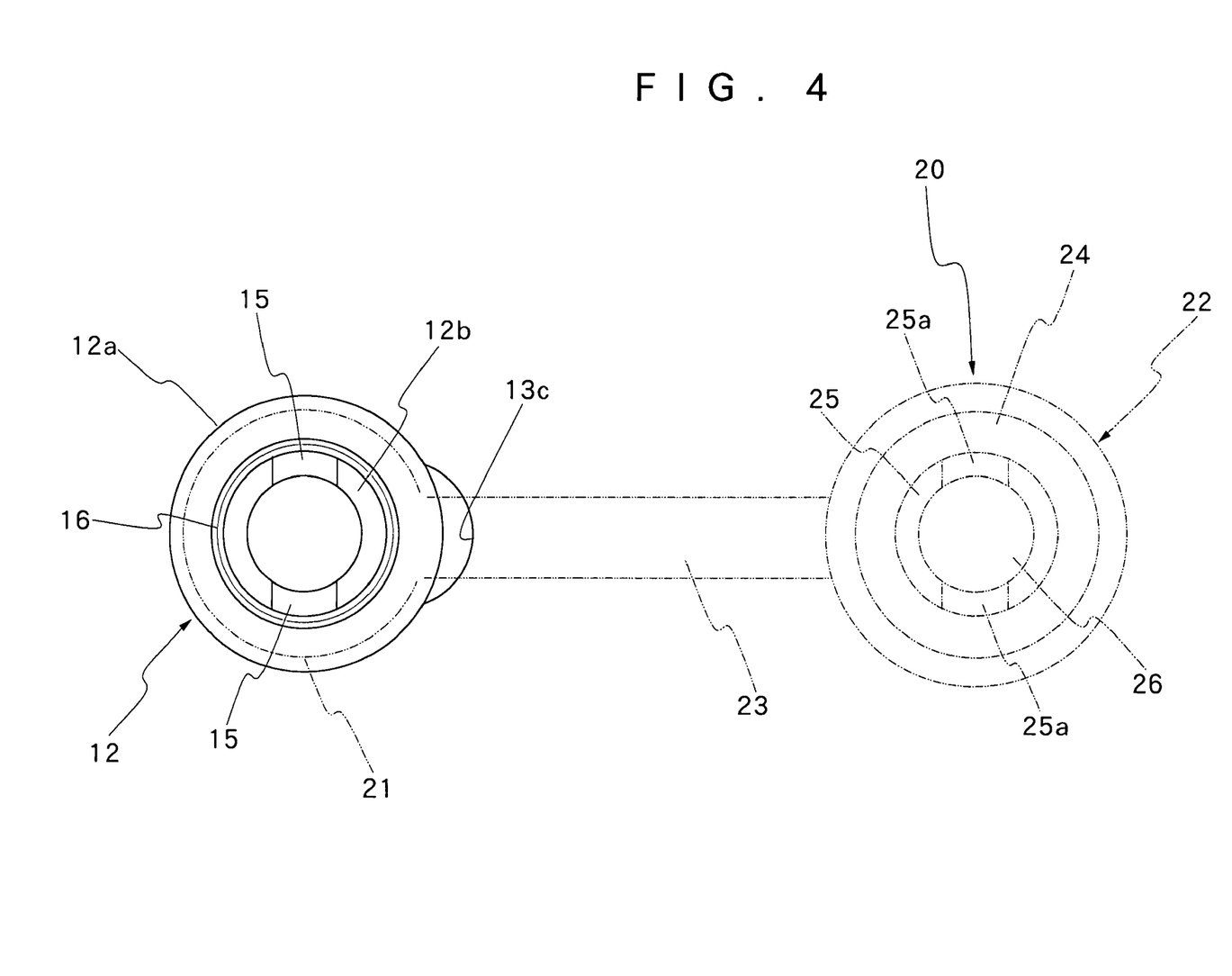
FIG. 4 is a plan view of the plug member, unplugged from the mouth piece of the liquid feed port and shown by imaginary line.
Figure 5:
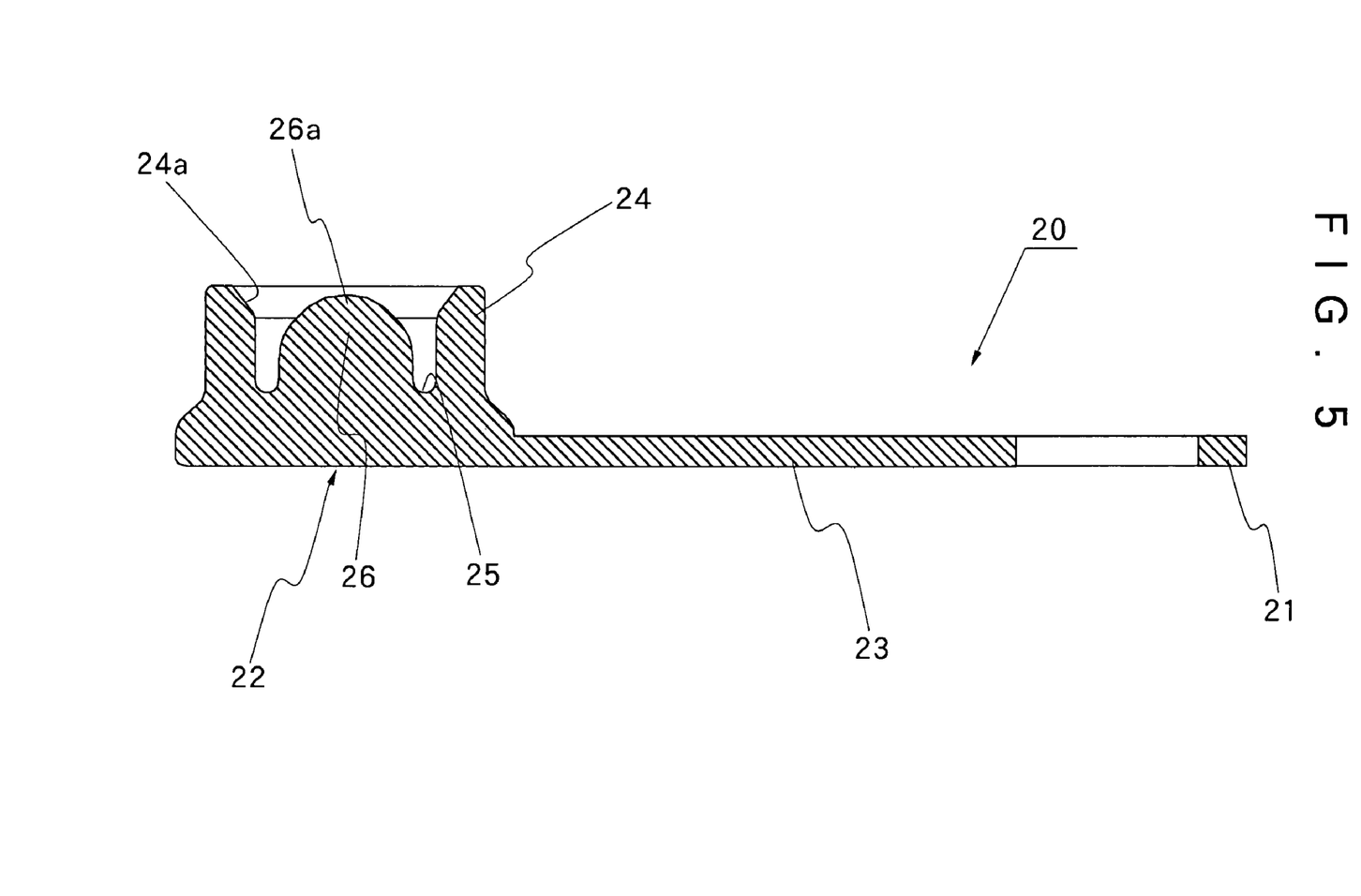
FIG. 5 is a schematic sectional view of the plug member.

The plug member 20 as a whole is formed of a resilient material such as fluorine rubber or the like, and integrally has circular structures at the opposite ends of a narrow strip as indicated by imaginary line in FIG. 4 and shown in a sectional view in FIG. 5. More particularly, the plug member 20 is constituted by a main body portion 22, and a connector hook ring 21 to be fitted around the mouth piece 12 before fitting the main body 22 on the mouth piece of the liquid feed port 10. The connector hook ring 21 is connected with the main body 22 through a flexible connecting strip 23. The connector hook ring 21 is arranged to have an inside diameter smaller than outside diameter of the Luer-Lok portion 12d of the mouth piece 12, so that it can be tightly fitted on and around the mount piece 12. Accordingly, the connector hook ring 21 is stretched to a larger diameter at the time of riding over the male screw portion 16 and retained in position in a gripped state between the stepped wall surface 13a of the nest hole 13 and the male screw portion 16 of the mouth piece 12.

The nest hole 13 is provided with a cylindrical riser wall 13b around the stepped surface 13a. Diameter of this cylindrical riser wall 13b is larger than the outside diameter of the connector hook ring 21, and a stepped wall 13c of a predetermined width in the circumferential direction is provided at one position on the inner side of the riser wall 13b for orientation of the plug member 20. Namely, the stepped wall portion 13c is in the form of an arcuate segment having a length slightly larger than the width of the connecting strip 23 of the plug member 20. When the plug member 20 is fitted on the mouth piece 12 of the liquid feed port 10, the connecting strip 23 of the plug member 20 is guided by opposite side walls of the stepped wall portion 13c to set the plug member in a right direction relative to the mouth piece 12.

The main body 22 of the plug member 20 is largely constituted by an annular outer wall portion 24, a hemispherical dome-like inner wall portion 26 and an annular groove 25 which is formed between the outer and inner wall portions 24 and 26. The annular groove 25 is arranged to have a smaller width as compared with the thickness of the Luer-Lok portion 12d of the mouth piece 12. Therefore, as the main body 22 of the plug member 20 is fitted on the mouth piece 12, the Luer-Lok portion 12d is tightly gripped in the annular groove 25 or between the outer and inner walls portions 24 and 26 on the main body 22 of the plug member 20. As a consequence, the mouth piece 12 at the liquid feed port 10 is hermetically closed by the plug member 20. In this instance, the pendant outer wall portion 24 is arranged to have a sufficient length for completely covering the male screw portion 16 of the mouth piece 12. Therefore, the outer wall portion 24 of the plug member 20 is pushed against and gripped by screw threads of the male screw portion 16 in such a way as to prevent dislocation of the plug member off the mouth piece 12. Further, the notched grooves 15 on the outer end of the Luer-Lok portion 12d are brought into engagement with projections 25a which are provided in corresponding positions at the bottom of the annular groove 25.

Having the structure as described above, the plug member 20 has its connector hook ring 21 constantly fitted and kept on the mouth piece 12 of the liquid feed port 10. The liquid feed port 10 is hermetically closed as soon as the main body 22 of the plug member 20 is fitted on the mouth piece 12. When the main body 22 of the plug member 20 is removed from the mouth piece 12, the liquid feed adaptor 30 can be connected to the mouth piece 12. Even if the main body 22 is removed from the mouth piece 12, the plug member 20 itself is still retained in a connected state by way of the connector hook ring 21. Further, as the main body 22 is fitted on the mouth piece 12, the connecting strip 23 is guided by opposite side walls of the stepped wall portion 13b to orient the main body 22 constantly into a right position relative to the proximal end of the mouth piece 12 without making deviating rotational movements. Accordingly, the notched grooves 15 on the proximal end face of the Luer-Lok portion 12d can be oriented toward and brought into engagement with the projections 25a at the bottom of the annular groove 25 on the main body portion 22. As a result, the proximal end of the Luer-Lok portion 12d is hermetically closed by the main body portion 22 of the plug member 20. In cooperation with a tapered surface 24a which is provided on the inner periphery of the outer wall portion 24 of the main body 22, the dome-like round top end portion 26a of the inner wall 26 functions to guide and bring the annular groove 25 into engagement with the Luer-Lok portion 12d upon fitting the main body 22 of the plug member 20 on the mouth piece 12.

Figure 6:
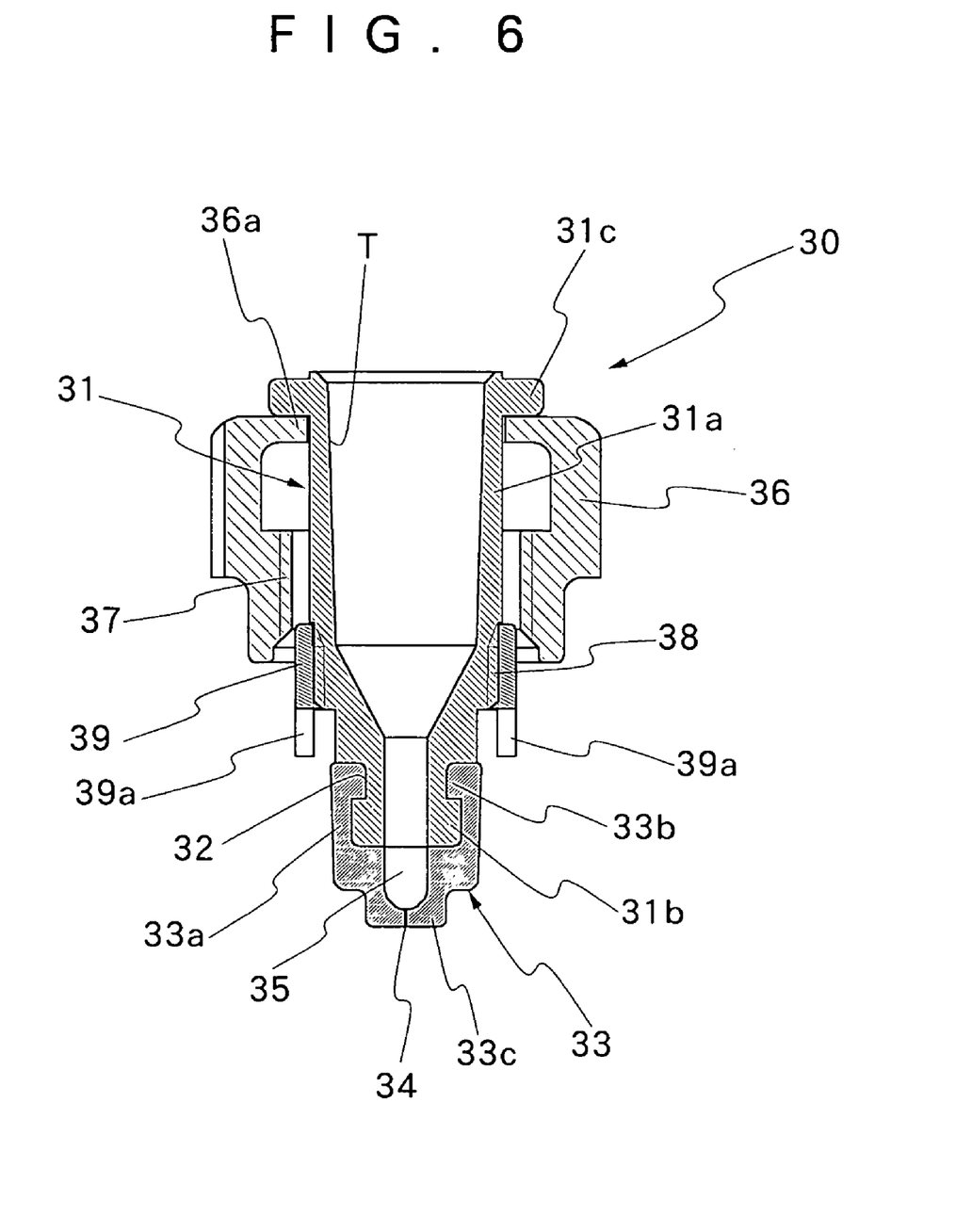
FIG. 6 is a schematic sectional view of the liquid feed adaptor.

When there arises a necessity for feeding a certain liquid to a body cavity, the main body 22 of the plug member 20 is removed from the Luer-Lok portion 12d of the mouth piece 12, and instead the liquid feed adaptor 30 is connected to the mouth piece 12 as shown in FIG. 3. In this state, a required liquid is fed toward the liquid feed passage 11 from a syringe which is connected to a Luer-Lok member 31 on the liquid feed adaptor 30. As shown in FIG. 6, the Luer-Lok member 31 of the liquid feed adaptor 30 is provided with a Luer=Lok taper surface T, similar to the one which is provided on the inner periphery of the Luer-Lok portion 12d of the mouth piece 12. On the outer peripheral side, the Luer-Lok member 31 is provided with a large diameter portion 31a and a small diameter portion 31b at its outer and inner ends, respectively. An annular fitting groove 32 is formed around the outer periphery of the Luer-Lok member 31 immediately on the proximal side of the small diameter portion 31b.

The Luer-Lok member 31 is opened toward the mouth piece 12 at its fore or inner end and communicated with the liquid feed passage 11 through the mouth piece 12. However, if the Luer-Lock member 31 is constantly in communication with the liquid feed passage 11, reverse flows will occur in the liquid feed passage 11 when no syringe or other pressurized liquid feed means is connected. In order to prevent such reverse flows, a check valve member 33 is attached to the small diameter portion 31b of the Luer-Lok member 31. In this instance, the check valve 33 is formed of a heat-resistant resilient material like silicon rubber, and tubular in general shape. More specifically, the check valve member 33 is provided with a fitting body portion 33a on the side of the proximal or outer end of its tubular body, to be assembled with the Luer-Lok member 31 by fitting engagement with a fore end portion of the latter. In the particular embodiment shown, the fitting body portion 33a is arranged to embrace the small diameter portion 31b of the Luer-Lok member 31. Further, at the outer end, the check valve member 33 is provided with an annular rim33b on and around its inner periphery for fitting engagement with the annular groove 32 on the side of the Luer-Lok member 31. In this regard, it is desirable to fit the check valve member 33 on the Luer-Lok member 31 by way of insert molding. The diameter of the tubular body of the check valve member 33 is reduced stepwise in a front end portion to form a reduced diameter portion 33c on the front side of the fitting portion 33a. The distal end face of the reduced diameter portion 33c is closed, and a slit 34 is provided in this distal end face to function as a check valve. Further, in communication with the internal passage of the Luer-Lok member 31, a passage 35 is formed to extend as far as the slit 34 and axially through the small diameter portion 31b and the reduced diameter portion 33c. Thus, normally meeting ends of the slit 34 are tightly closed to each other block communication between the Luer-Lok member 31 and the mouth piece 12 of the liquid feed port 10 unless internal pressure of the Luer-Lok member 31 becomes higher than internal pressure of the mouth piece 12. Further, when a liquid is supplied under high pressure from a syringe or other pressurized liquid feed means which is connected to the Luer-Lok member 31, the slit 34 is opened as soon as the high liquid pressure is introduced into the passage 35 to permit supply of the liquid to the liquid supply passage 11 through the mouth piece 12 of the liquid feed port 10.

The liquid feed adaptor 30 is attached and detached to and from the mouth piece 12 of the liquid feed port 10 through a mechanism as described below. The liquid feed adaptor 30 is fixedly set on the mouth piece 12 by a nut member 36 which is fitted on the large diameter portion 31a of the Luer-Lok member 31. In this instance, the nut member 36 is provided with a female screw portion 37 on the inner periphery of its fore end portion for threaded engagement with the male screw portion 16 which is provided on the outer periphery of the mouth piece 12. Similarly to the male screw portion 16, the female screw portion is in the form of a multiple thread screw. Provided at the outer end of the nut member 36 is an inwardly projecting rim 36a which has an inside diameter slightly larger than the outside diameter of the large diameter portion 31a of the Luer-Lok member 31. That is to say, the nut member 36 is loosely and rotatably fitted on the large diameter portion 31a of the Luer-Lok member 31.

Figure 7:
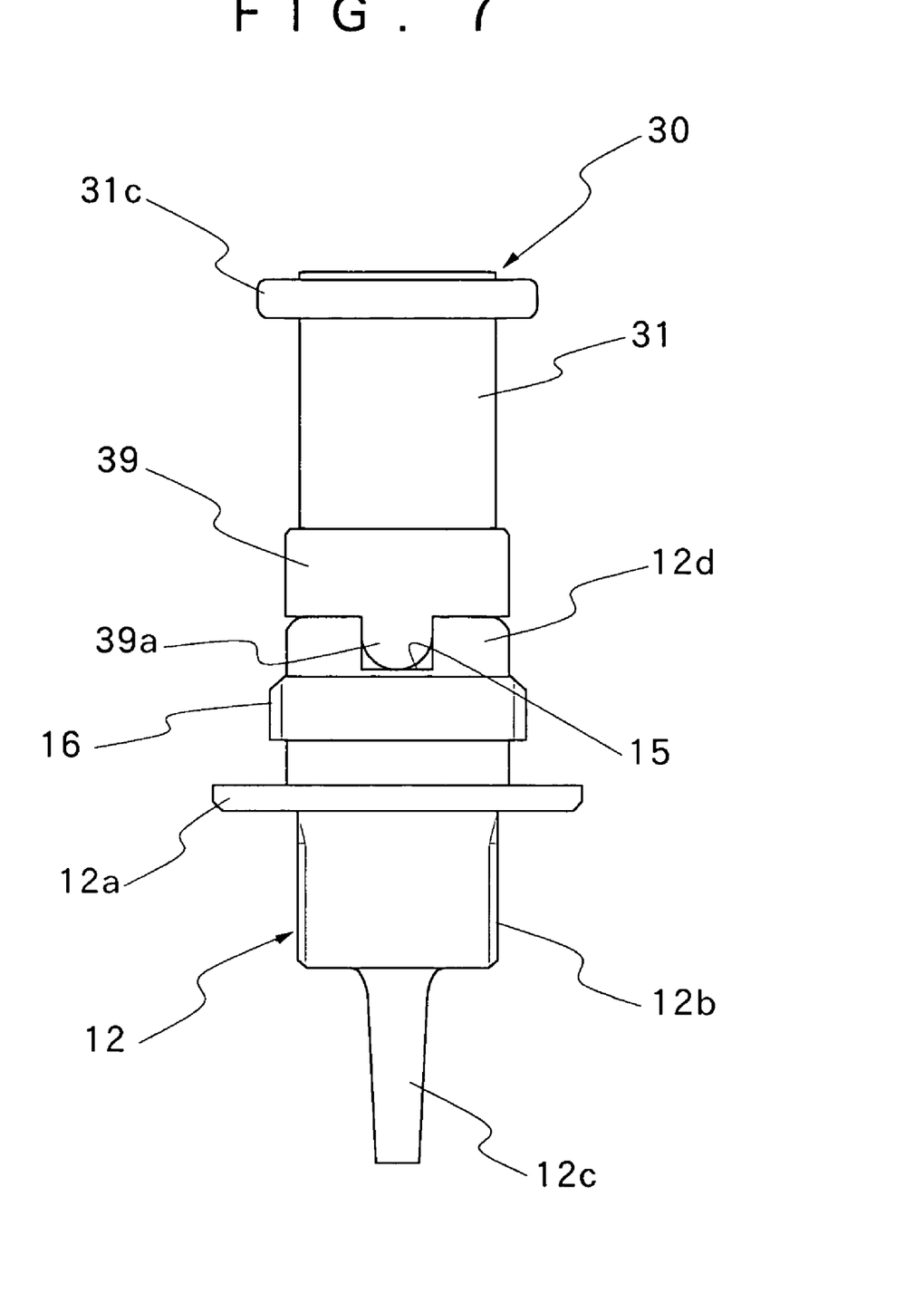
FIG. 7 is a schematic front view of the liquid feed adaptor which is fitted on the mouth piece, with a nut member omitted for the convenience of illustration.

Further, the Luer-Lok member 31 is provided with an external male screw at the lower or inner end of the large diameter portion 31a. A stopper ring 39 of a predetermined thickness is threaded on the male screw 38 and fixedly bonded to the latter by the use of a heat-resistant adhesive. The stopper ring 39 is arranged to have an outside diameter larger than the inside diameter of the inwardly projecting rim 36a. Furthermore, a flange 31c is provided around an outer or proximal end portion of the Luer-Lok member 31c. This flange 31c is adapted to receive and engage with a coupling portion of a syringe when the latter is connected to the Luer-Lok member 31. Besides, the flange 31c is arranged to have an outside diameter which is larger than inside diameter of the inwardly projecting 36a of the nut member 36. It follows that the nut member 36 is loosely and rotatably fitted on the large diameter portion 31a of the Luer-Lok member 31. The inwardly projecting rim 36a of the nut member 36 is movable in the axial direction between the stopper ring 39 and the flange 31c on the Luer-Lok member 31, but the nut member 36 is prevented from getting separated from the Luer-Lok member 31. Furthermore, the stopper ring 39 is provided with axial projections 39a on its fore end face. These axial projections 39a are brought into engagement with the notched grooves 15 on the side of the mouth piece 12 to prevent rotational movements of the Luer-Lok member 31 even if a force is applied thereto in a rotational direction at the time of connecting a syringe or the like. Edges of the axial projections 39a are rounded off in a convexly arcuate shape thereby to urge the axial projections into engagement with the notched grooves 15 on the side of the mouth piece 12.

Being arranged in the manner as described above, the liquid feed adaptor 30 can be detachably fitted on the mouth piece 12 of the liquid feed port 10 in place of the main body portion 22 of the plug member 20. For this purpose, firstly the nut member 36 is displaced toward an outer position on the side of the flange portion 31c of the Luer-Lok, and then the check valve member 33 which is assembled with the Luer-Lok member 31 is fitted into the Luer-Lok portion 12d of the mouth piece 12. The Luer-Lok portion 12d is provided with the Luer-Lok taper surface T on its inner periphery and continuously reduced in diameter toward its fore end. On the other hand, the fitting portion 33a of the check valve member 33 has an outside diameter which is substantially same as or slightly smaller than the inside diameter at the proximal end of the Luer-Lok portion 12d. Accordingly, as the fitting portion 33a of the check valve member 33 undergoes compressive resilient deformation as it is admitted into the Luer-Lok portion 12 and moved inward along the Luer-Lok taper surface T on the inner periphery of the Luer-Lok portion 12d. As a result, the outer peripheral surface of the Luer-Lok member 31 of the liquid feed adaptor 30 is engaged with the inner peripheral surface of the Luer-Lok portion 12d in a hermetically closed state.

Further, at the time of connecting the Luer-Lok member 31 to the mouth piece 12 of the liquid feed port 10, the axial projections 39a at the inner end of the stopper ring 39 are brought into engagement with the notched grooves 15 on the outer end face of the Luer-Lok portion 12d. As a result, the Luer-Lok member 31 which is securely fixed to the stopper ring 39 is blocked against rotational movements. Since the fore ends of the axial projections 39a are rounded into a convexly arcuate shape, these projections 39a can be easily urged to fall into engagement with the notched grooves 15 by turning the Luer-Lok member 31 as it is pushed into the Luer-Lok portion 12d of the mouth piece 12. Further, as long as the axial projections 39a are not engaged with the notched grooves 15, that is to say, as long as the axial projections 39a are riding on outer end face portions other than the notched grooves 15 of the Luer-Lok portion 12d, the female screw portion 37 of the nut member 36 is unable to get into threaded engagement with the male screw portion 16 which is provided on the side of the mouth piece 12.

After placing the liquid feed adaptor 30 to a predetermined depth within the mouth piece 12 of the liquid feed port 10, the female screw portion 37 of the nut member 36 is threaded onto the male screw portion 16 on the side of the mouth piece 12 to fix the liquid feed adaptor 30 on the mouth piece 12 in a connected state. In this instance, since both of the female screw portion 37 and the male screw portion 16 are a multiple thread screw, they can be threaded to a predetermined extent simply by turning the nut member 36 one or a few number of times. As the female screw portion 37 is threaded onto the male screw portion 16, the fore or inner end of the nut member 36 is pressed against the connector hook ring 21 of the plug member 20 to cause a certain degree of compressive deformation to the connector hook ring 21. As a consequence, the connector hook ring 21 of the plug member 20 functions to prevent spontaneous rotational movements of the nut member 36.

When the liquid feed adaptor 30 is connected to the mouth piece 12 of the liquid feed port 10 in the manner as described above, the slit 34 of the check valve member 33 is in a closed state, and its clinch portion 33a is pressed against the Luer-Lok portion 12d of the mouth piece 12 in a resiliently deformed state to preclude possibilities of reverse liquid flows from the side of the liquid feed passage 11.

For example, a syringe is connected to the Luer-Lok member 31 thereby to feed water for washing intracavitary walls or to sprinkle a medicinal solution in a body cavity. At the time of connecting a syringe, it is turned like a screw relative to the Luer-Lok member 31. By so doing, the syringe is tightly engaged with the Luer-Lok taper surface T within the Luer-Lok member 31 and securely fixed to the latter by holding the flange portion 31c. Upon operating the syringe to send a liquid forward under pressure, the slit 34 of the check valve member is opened to supply the liquid into the liquid feed passage 11 through the mouth piece 12. As a result, a jet of the liquid is injected into a body cavity from the liquid injection port 11a. Upon completing injection of the liquid, the syringe is separated from the Luer-Lok member 31 by turning the syringe as if it were unscrewed from the Luer-Lok member 31. In this manner, a rotational force is applied to the Luer-Lok member 31 at the time of mounting or dismantling a syringe. However, since the axial projections 39a on the stopper ring 39 are engaged with the notched grooves 15 on the side of the mouth piece 12, there is no possibility of the Luer-Lok member 31 being rotated on such an occasion.

Therefore, when there arises a necessity for feeding a liquid to a body cavity while operating an endoscope, the liquid feed adaptor 30 is attached to the mouth piece 12 of the liquid feed port 10. In a case where there is no need for supplying a liquid, the liquid feed adaptor 30 is detached and, in place of the adaptor 30, the main body portion 22 of the plug member 20 is fitted on the mouth piece 12 over its connector hook ring 21 which is constantly hooked on the mouth piece 12.

After using an endoscope, the liquid feed passage 11 including the liquid injection port 11a has to be washed clean. At the time of washing the liquid feed passage 11, neither the main body 22 of the plug member 20 nor the liquid feed adaptor 30 is attached to the Luer-Lok portion 12d of the mouth piece 12. A syringe of a cleaning solution or wash water and then a syringe of a disinfectant are connected to the Luer-Lok portion 12d. At this time, the syringes can be easily connected to the Luer-Lok portion 12d because the Luer-Lok taper surface T is provided on the inner periphery of the Luer-Lok poriton 12d similarly to the Luer-Lok member 31. Besides, the liquid feed passage 11 can be washed quite smoothly since there is no obstacles to liquid flows in the entire length of the liquid feed passage 11 from the Luer-Lok portion 12d to the liquid injection port 11a. If the male screw portion 16 is exposed on the outer periphery of the mouth piece 12, it may touched by a hand of a handling person during the washing operation. However, the male screw portion 16 is circumvented by the riser wall 13b of the nesting hole 13 in the casing 1a of the manipulating head assembly 1 of the endoscope, there is no possibility of the male screw portion 16 coming into contact with a hand of a handling person. Further, the liquid feed adaptor 30 also needs washing after use. In this regard, disinfection in an autoclave is possible in a case where the Luer-Lok member 31, nut member 36 and stopper ring 39 of the liquid feed adaptor 30 are of stainless steel, the check valve member 33 is of heat-resistant resilient material, and the stopper ring 39 is fixedly bonded to the Luer-Lok member 31 by the use of a heat-resistant adhesive.

What is claimed is:

1. An endoscopic liquid feed device, said liquid feed device including a liquid feed port provided on a casing of a manipulating head assembly of an endoscope in communication with an internal liquid feed passage leading to a liquid injection port opened at a fore distal end portion of an insertion tube of said endoscope, and a mouth piece provided fixedly at said liquid feed port for detachably connecting a liquid feed adaptor to said liquid feed port at the time of feeding a liquid to said liquid injection port from a pressurized liquid feed means connected to said liquid feed adaptor, characterized in that:

a liquid feed adaptor is constituted by a Luer-Lok member having a check valve member fitted on a fore end portion thereof, a stopper ring provided on outer periphery of said Luer-Lok member, and a nut member rotatably fitted on said Luer-Lok member and axially movable between said stopper ring and a flange portion provided at an outer proximal end of said Luer-Lok member;

a mouth piece being provided with an external male screw portion on outer peripheral side thereof for threaded engagement with said nut member, and formed with a Luer-Lok portion on inner peripheral side thereof, said Luer-Lok portion having a gradually diminishing inside diameter in forward direction; and a pressurized liquid feed means such as a syringe being detachably connectible to said Luer-Lok portion of said mouth piece in place of said liquid feed adaptor.

2. An endoscopic liquid feed device as defined in claim 1, further comprising a plug member adapted to be detachably connected to said mouth piece of a liquid feed port in place of said liquid feed adaptor.

3. An endoscopic liquid feed device as defined in claim 2, wherein said plug member is formed of a resilient material and constituted by a generally tubular main body portion adapted to be detachably fitted on said mouth piece, a hook ring portion adapted to be constantly hooked on said mouth piece, and a flexible narrow strip portion connecting said hook ring portion to said main body portion.

4. An endoscopic liquid feed device as defined in claim 3, wherein said liquid feed adaptor is arranged to be connected to said mouth piece of said liquid feed port in overlapping relation with said hook ring portion of said plug member.

5. An endoscopic liquid feed device as defined in claim 4, wherein said nut member of said liquid feed adaptor is arranged to seat on said hook ring portion of said plug member, causing compressive deformation to said hook ring portion.

6. An endoscopic liquid feed device as defined in claim 1, wherein said check valve member is formed of a heat-resistant resilient material, and provided with a slit in a fore end face thereof.

7. An endoscopic liquid feed device as defined in claim 6, wherein said check valve member is formed integrally with said liquid feed adaptor by insert molding.

8. An endoscopic liquid feed device as defined in claim 7, wherein said check valve member is generally formed in a tubular shape having, on front side, an outside diameter substantially same as or larger than inside diameter of said Luer-Lok portion of said mouth piece.

9. An endoscopic liquid feed device as defined in claim 1, wherein said nut member and said external male screw portion on said Luer-Lok portion of said mouth piece are engaged with each other through multiple thread screws.

10. An endoscopic liquid feed device as defined in claim 1, wherein said Luer-Lok member is provided with a flange portion at an outer proximal end for engagement with a syringe connected thereto, and said nut member is provided with an inwardly projecting rim portion having an inside diameter smaller than outside diameters of said flange portion and said stopper ring to prevent said nut member from falling off.

11. An endoscopic liquid feed device as defined in claim 10, wherein said stopper ring is threaded on outer periphery of said Luer-Lok member and fixedly bonded to the latter by the use of an adhesive.

12. An endoscopic liquid feed device as defined in claim 11, wherein said stopper ring is engaged with a proximal end portion of said mouth piece of a liquid feed port through anti-rotational locking means.

* * * * *